United States Patent [19]

Dikstein et al.

[11] Patent Number: 5,710,025

[45] Date of Patent: Jan. 20, 1998

[54] CELL-TYPE SPECIFIC TRANSCRIPTION FACTOR

[75] Inventors: Rivka Dikstein, Rehovot, Israel; Robert Tjian, Berkeley, Calif.

[73] Assignee: The Regents of the University of California, Oakland, Calif.

[21] Appl. No.: 725,012

[22] Filed: Oct. 2, 1996

[51] Int. Cl.$^6$ .............................. C12P 21/02; C12N 1/21; C12N 5/10; C12N 15/12

[52] U.S. Cl. .................. 435/69.1; 435/172.3; 435/252.3; 435/325; 536/23.5; 536/24.3; 536/24.31

[58] Field of Search ................................ 536/24.3, 24.31, 536/23.5; 435/172.3, 69.1, 325, 252.3

*Primary Examiner*—George C. Elliott
*Assistant Examiner*—Johnny F. Railey II
*Attorney, Agent, or Firm*—Richard Aron Osman

[57] ABSTRACT

The invention provides methods and compositions relating to human tata-binding protein associated factor 105 (hTAF$_{II}$105) and related nucleic acids. The proteins may be produced recombinantly from transformed host cells from the disclosed hTAF$_{II}$105 encoding nucleic acids or purified from human cells. The invention provides isolated hTAF$_{II}$105 hybridization probes and primers capable of specifically hybridizing with the disclosed hTAF$_{II}$105 gene, hTAF$_{II}$105-specific binding agents such as specific antibodies, and methods of making and using the subject compositions in diagnosis, therapy and in the biopharmaceutical industry.

13 Claims, No Drawings

5,710,025

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 2556 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 1..2403

( x i ) SEQUENCE DESCRIPTION: SEQ ID NO:1:

```
GGG  ACC  CTG  GTG  ACC  AAA  GTG  GCT  CCG  GTC  AGC  GCC  CCT  CCT  AAA  GTC        48
Gly  Thr  Leu  Val  Thr  Lys  Val  Ala  Pro  Val  Ser  Ala  Pro  Pro  Lys  Val
 1              5                        10                      15

AGC  AGC  GGC  CCT  AGG  CTG  CCT  GCT  CCT  CAG  ATA  GTC  GCC  GTG  AAA  GCC        96
Ser  Ser  Gly  Pro  Arg  Leu  Pro  Ala  Pro  Gln  Ile  Val  Ala  Val  Lys  Ala
             20                       25                      30

CCC  AAC  ACC  ACG  ACA  ATC  CAG  TTT  CCT  GCT  AAT  TTG  CAG  CTT  CCT  CCA       144
Pro  Asn  Thr  Thr  Thr  Ile  Gln  Phe  Pro  Ala  Asn  Leu  Gln  Leu  Pro  Pro
         35                       40                      45

GGA  ACC  GTT  TTG  ATT  AAA  AGT  AAC  AGT  GGT  CCG  TTG  ATG  TTG  GTA  TCT       192
Gly  Thr  Val  Leu  Ile  Lys  Ser  Asn  Ser  Gly  Pro  Leu  Met  Leu  Val  Ser
     50                       55                      60

CCT  CAG  CAA  ACT  GTA  ACA  AGA  GCC  GAG  ACC  ACA  AGT  AAC  ATA  ACC  TCA       240
Pro  Gln  Gln  Thr  Val  Thr  Arg  Ala  Glu  Thr  Thr  Ser  Asn  Ile  Thr  Ser
 65                       70                      75                      80

AGG  CCA  GCA  GTA  CCA  GCG  AAT  CCT  CAA  ACA  GTC  AAA  ATC  TGT  ACA  GTG       288
Arg  Pro  Ala  Val  Pro  Ala  Asn  Pro  Gln  Thr  Val  Lys  Ile  Cys  Thr  Val
                     85                       90                      95

CCG  AAC  TCT  AGC  TCA  CAA  TTA  ATC  AAG  AAA  GTG  GCA  GTG  ACA  CCT  GTT       336
Pro  Asn  Ser  Ser  Ser  Gln  Leu  Ile  Lys  Lys  Val  Ala  Val  Thr  Pro  Val
                100                      105                     110

AAA  AAA  TTG  GCA  CAA  ATA  GGA  ACT  ACT  GTG  GTA  ACC  ACT  GTT  CCG  AAG       384
Lys  Lys  Leu  Ala  Gln  Ile  Gly  Thr  Thr  Val  Val  Thr  Thr  Val  Pro  Lys
            115                      120                     125

CCT  TCC  TCA  GTA  CAA  TCT  GTG  GCT  GTG  CCA  ACC  AGT  GTC  GTC  ACA  GTT       432
Pro  Ser  Ser  Val  Gln  Ser  Val  Ala  Val  Pro  Thr  Ser  Val  Val  Thr  Val
        130                      135                     140

ACT  CCT  GGA  AAG  CCA  TTG  AAT  ACT  GTA  ACT  ACC  CTG  AAG  CCT  TCA  AGT       480
Thr  Pro  Gly  Lys  Pro  Leu  Asn  Thr  Val  Thr  Thr  Leu  Lys  Pro  Ser  Ser
145                      150                      155                     160

TTG  GGA  GCA  TCA  TCC  ACT  CCT  TCA  AAT  GAG  CCC  AAT  CTT  AAA  GCA  GAG       528
Leu  Gly  Ala  Ser  Ser  Thr  Pro  Ser  Asn  Glu  Pro  Asn  Leu  Lys  Ala  Glu
                     165                      170                     175

AAC  TCA  GCA  GCT  GTT  CAG  ATT  AAT  CTT  TCT  CCG  ACA  ATG  CTA  GAA  AAT       576
```

```
                Asn Ser Ala Ala Val Gln Ile Asn Leu Ser Pro Thr Met Leu Glu Asn
                                180                 185                 190

GTG AAG AAA TGC AAG AAC TTC CTT GCA ATG TTA ATA AAA CTA GCA TGT                 624
Val Lys Lys Cys Lys Asn Phe Leu Ala Met Leu Ile Lys Leu Ala Cys
        195                 200                 205

AGT GGA TCA CAG TCC CCT GAA ATG GGG CAA AAT GTG AAG AAG CTG GTG                 672
Ser Gly Ser Gln Ser Pro Glu Met Gly Gln Asn Val Lys Lys Leu Val
        210                 215                 220

GAA CAA CTT TTG GAT GCA AAA ATC GAA GCA GAA GAA TTT ACT AGG AAA                 720
Glu Gln Leu Leu Asp Ala Lys Ile Glu Ala Glu Glu Phe Thr Arg Lys
225                 230                 235                 240

CTG TAT GTT GAA CTC AAG TCT TCA CCT CAG CCT CAC CTG GTT CCT TTT                 768
Leu Tyr Val Glu Leu Lys Ser Ser Pro Gln Pro His Leu Val Pro Phe
                245                 250                 255

CTT AAG AAA AGC GTG GTT GCC TTA CGA CAA CTT CTG CCT AAC TCC CAG                 816
Leu Lys Lys Ser Val Val Ala Leu Arg Gln Leu Leu Pro Asn Ser Gln
        260                 265                 270

AGC TTC ATC CAG CAA TGT GTT CAG CAG ACT TCT AGT GAC ATG GTC ATT                 864
Ser Phe Ile Gln Gln Cys Val Gln Gln Thr Ser Ser Asp Met Val Ile
        275                 280                 285

GCT ACC TGT ACT ACA ACA GTA ACA ACT TCT CCT GTG GTG ACA ACT ACA                 912
Ala Thr Cys Thr Thr Thr Val Thr Thr Ser Pro Val Val Thr Thr Thr
        290                 295                 300

GTG TCC TCA AGC CAG TCT GAA AAG TCA ATT ATT GTT TCT GGA GCA ACA                 960
Val Ser Ser Ser Gln Ser Glu Lys Ser Ile Ile Val Ser Gly Ala Thr
305                 310                 315                 320

GCA CCC AGA ACT GTG TCA GTG CAA ACT TTG AAC CCA CTT GCT GGT CCA                1008
Ala Pro Arg Thr Val Ser Val Gln Thr Leu Asn Pro Leu Ala Gly Pro
                325                 330                 335

GTG GGA GCA AAA GCT GGA GTT GTG ACA CTT CAT TCT GTG GGC CCA ACT                1056
Val Gly Ala Lys Ala Gly Val Val Thr Leu His Ser Val Gly Pro Thr
        340                 345                 350

GCT GCA ACA GGA GGA ACA ACA GCT GGA ACT GGT TTG CTT CAG ACT TCA                1104
Ala Ala Thr Gly Gly Thr Thr Ala Gly Thr Gly Leu Leu Gln Thr Ser
        355                 360                 365

AAA CCA CTT GTG ACA TCT GTG GCA AAC ACA GTG ACC ACG GTC TCA CTG                1152
Lys Pro Leu Val Thr Ser Val Ala Asn Thr Val Thr Thr Val Ser Leu
370                 375                 380

CAA CCT GAA AAG CCA GTT GTC TCT GGA ACA GCA GTA ACA CTG TCC CTT                1200
Gln Pro Glu Lys Pro Val Val Ser Gly Thr Ala Val Thr Leu Ser Leu
385                 390                 395                 400

CCA GCA GTA ACT TTT GGA GAA ACT TCA GGT GCA GCT ATT TGT CTT CCA                1248
Pro Ala Val Thr Phe Gly Glu Thr Ser Gly Ala Ala Ile Cys Leu Pro
                405                 410                 415

TCT GTG AAA CCT GTT GTT TCC TTC TGC TGG GAC CAC ATC TGC AAG CCT                1296
Ser Val Lys Pro Val Val Ser Phe Cys Trp Asp His Ile Cys Lys Pro
        420                 425                 430

GTT ATT GGG ACT CCA GTT CAA ATC AAA CTT GCC CAG CCG GGC CCT GTC                1344
Val Ile Gly Thr Pro Val Gln Ile Lys Leu Ala Gln Pro Gly Pro Val
        435                 440                 445

CTT TCA CAA CCA GCT GGG ATT CCA ACA GGC AGT TCA AGC AAG CAA CTA                1392
Leu Ser Gln Pro Ala Gly Ile Pro Thr Gly Ser Ser Ser Lys Gln Leu
        450                 455                 460

TTC TCA TTG TTT CAC GTA GTT CAG CAG CCT TCA GGA GGC AAT GAA AAA                1440
Phe Ser Leu Phe His Val Val Gln Gln Pro Ser Gly Gly Asn Glu Lys
465                 470                 475                 480

CAA GTG ACC ACA ATT TCA CAT TCC TCA ACA TTG ACC ATT CAG AAA TGT                1488
Gln Val Thr Thr Ile Ser His Ser Ser Thr Leu Thr Ile Gln Lys Cys
                485                 490                 495

GGA CAG AAG ACG ATG CCA GTG AAC ACC ATA ATA CCT ACT AGT CAG TTT                1536
```

```
Gly Gln Lys Thr Met Pro Val Asn Thr Ile Ile Pro Thr Ser Gln Phe
            500             505             510

CCT CCA GCT TCC ATT CTA AAG CAA ATT ACT CTG CCT GGA AAT AAA ATT        1584
Pro Pro Ala Ser Ile Leu Lys Gln Ile Thr Leu Pro Gly Asn Lys Ile
            515             520             525

CTG TCA CTT CAA GCA TCT CCT ACT CAG AAA AAT AGA ATA AAA GAG AAT        1632
Leu Ser Leu Gln Ala Ser Pro Thr Gln Lys Asn Arg Ile Lys Glu Asn
            530             535             540

GTA ACA TCA TGC TTC CGA GAT GAG GAT GAC ATC AAT GAT GTG ACT TCT        1680
Val Thr Ser Cys Phe Arg Asp Glu Asp Asp Ile Asn Asp Val Thr Ser
545             550             555             560

ATG GCA GGG GTC AAC CTT AAT GAA GAA AAT GCC TGC ATC TTA GCA ACA        1728
Met Ala Gly Val Asn Leu Asn Glu Glu Asn Ala Cys Ile Leu Ala Thr
                565             570             575

AAC TCT GAA TTG GTT GGC ACA CTC ATT CAG TCA TGT AAA GAT GAA CCA        1776
Asn Ser Glu Leu Val Gly Thr Leu Ile Gln Ser Cys Lys Asp Glu Pro
            580             585             590

TTT CTT TTT ATT GGA GCT CTA CAA AAG AGA ATC TTA GAC ATT GGT AAA        1824
Phe Leu Phe Ile Gly Ala Leu Gln Lys Arg Ile Leu Asp Ile Gly Lys
            595             600             605

AAG CAT GAC ATT ACA GAA CTT AAC TCT GAT GCT GTG AAC TTG ATC TCC        1872
Lys His Asp Ile Thr Glu Leu Asn Ser Asp Ala Val Asn Leu Ile Ser
            610             615             620

CAA GCA ACA CAG GAA CGA CTA CGA GGC CTT CTA GAA AAA CTG ACT GCA        1920
Gln Ala Thr Gln Glu Arg Leu Arg Gly Leu Leu Glu Lys Leu Thr Ala
625             630             635             640

ATT GCT CAG CAT CGA ATG ACT ACT TAC AAG GCA AGT GAA AAT TAC ATC        1968
Ile Ala Gln His Arg Met Thr Thr Tyr Lys Ala Ser Glu Asn Tyr Ile
                645             650             655

CTG TGT AGT GAT ACC AGG TCA CAG CTC AAA TTT CTT GAA AAG CTG GAT        2016
Leu Cys Ser Asp Thr Arg Ser Gln Leu Lys Phe Leu Glu Lys Leu Asp
            660             665             670

CAA TTG GAG AAG CAG AGA AAG GAT TTG GAA GAA AGA GAA ATG TTA CTT        2064
Gln Leu Glu Lys Gln Arg Lys Asp Leu Glu Glu Arg Glu Met Leu Leu
            675             680             685

AAG GCA GCC AAG AGT CGT TCT AAT AAA GAA GAT CCA GAA CAG CTG AGA        2112
Lys Ala Ala Lys Ser Arg Ser Asn Lys Glu Asp Pro Glu Gln Leu Arg
            690             695             700

TTA AAG CAG AAA GCC AAA GAG TTA CAG CAA TTG GAA CTT GCA CAG ATA        2160
Leu Lys Gln Lys Ala Lys Glu Leu Gln Gln Leu Glu Leu Ala Gln Ile
705             710             715             720

CAG CAT AGA GAC GCT AAT CTC ACA GCT CTT GCA GCT ATT GGA CCA AGG        2208
Gln His Arg Asp Ala Asn Leu Thr Ala Leu Ala Ala Ile Gly Pro Arg
                725             730             735

AAG AAG AGA CCA CTA GAA TCT GGA ATT GAG GGC TTA AAA GAC AAC CTT        2256
Lys Lys Arg Pro Leu Glu Ser Gly Ile Glu Gly Leu Lys Asp Asn Leu
            740             745             750

CTT GCT TCT GGG ACA TCC AGC CTG ACA GCC ACC AAA CAG TTG CAT CGT        2304
Leu Ala Ser Gly Thr Ser Ser Leu Thr Ala Thr Lys Gln Leu His Arg
            755             760             765

CCA AGA ATC ACG AGA ATC TGC CTC AGG GAC TTG ATA TTT TGT ATG GAA        2352
Pro Arg Ile Thr Arg Ile Cys Leu Arg Asp Leu Ile Phe Cys Met Glu
            770             775             780

CAG GAA CGG GAG ATG AAG TAT TCT CGA GCT CTA TAC CTG GCC CTT CTG        2400
Gln Glu Arg Glu Met Lys Tyr Ser Arg Ala Leu Tyr Leu Ala Leu Leu
785             790             795             800

AAG TGACCACTCC ACTCTTCCAT CCACATCCTT GCTATTTACT GCCAAGAAG             2453
Lys

ACACAAAGCA TTGTTGCACT GTCCTGAAAT TTCAATTTCT GGAAAATAAC ACCAACATGA      2513
```

AAGAGCATTG TTTACGATTA GAACTTTATT AACTCTTACC TAT 2556

( 2 ) INFORMATION FOR SEQ ID NO:2:

( i ) SEQUENCE CHARACTERISTICS:
        ( A ) LENGTH: 801 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Gly Thr Leu Val Thr Lys Val Ala Pro Val Ser Ala Pro Pro Lys Val
 1               5                  10                  15

Ser Ser Gly Pro Arg Leu Pro Ala Pro Gln Ile Val Ala Val Lys Ala
            20                  25                  30

Pro Asn Thr Thr Thr Ile Gln Phe Pro Ala Asn Leu Gln Leu Pro Pro
        35                  40                  45

Gly Thr Val Leu Ile Lys Ser Asn Ser Gly Pro Leu Met Leu Val Ser
    50                  55                  60

Pro Gln Gln Thr Val Thr Arg Ala Glu Thr Thr Ser Asn Ile Thr Ser
65                  70                  75                  80

Arg Pro Ala Val Pro Ala Asn Pro Gln Thr Val Lys Ile Cys Thr Val
                85                  90                  95

Pro Asn Ser Ser Ser Gln Leu Ile Lys Lys Val Ala Val Thr Pro Val
            100                 105                 110

Lys Lys Leu Ala Gln Ile Gly Thr Thr Val Val Thr Val Pro Lys
        115                 120                 125

Pro Ser Ser Val Gln Ser Val Ala Val Pro Thr Ser Val Val Thr Val
    130                 135                 140

Thr Pro Gly Lys Pro Leu Asn Thr Val Thr Thr Leu Lys Pro Ser Ser
145                 150                 155                 160

Leu Gly Ala Ser Ser Thr Pro Ser Asn Glu Pro Asn Leu Lys Ala Glu
                165                 170                 175

Asn Ser Ala Ala Val Gln Ile Asn Leu Ser Pro Thr Met Leu Glu Asn
            180                 185                 190

Val Lys Lys Cys Lys Asn Phe Leu Ala Met Leu Ile Lys Leu Ala Cys
        195                 200                 205

Ser Gly Ser Gln Ser Pro Glu Met Gly Gln Asn Val Lys Lys Leu Val
    210                 215                 220

Glu Gln Leu Leu Asp Ala Lys Ile Glu Ala Glu Glu Phe Thr Arg Lys
225                 230                 235                 240

Leu Tyr Val Glu Leu Lys Ser Ser Pro Gln Pro His Leu Val Pro Phe
                245                 250                 255

Leu Lys Lys Ser Val Val Ala Leu Arg Gln Leu Leu Pro Asn Ser Gln
            260                 265                 270

Ser Phe Ile Gln Gln Cys Val Gln Gln Thr Ser Ser Asp Met Val Ile
        275                 280                 285

Ala Thr Cys Thr Thr Thr Val Thr Thr Ser Pro Val Val Thr Thr Thr
    290                 295                 300

Val Ser Ser Ser Gln Ser Glu Lys Ser Ile Ile Val Ser Gly Ala Thr
305                 310                 315                 320

Ala Pro Arg Thr Val Ser Val Gln Thr Leu Asn Pro Leu Ala Gly Pro
                325                 330                 335

Val Gly Ala Lys Ala Gly Val Val Thr Leu His Ser Val Gly Pro Thr
            340                 345                 350
```

| Ala | Ala | Thr | Gly | Gly | Thr | Thr | Ala | Gly | Thr | Gly | Leu | Leu | Gln | Thr | Ser |
|---|---|---|---|---|---|---|---|---|---|---|---|---|---|---|---|
| | | 355 | | | | | 360 | | | | | 365 | | | |
| Lys | Pro | Leu | Val | Thr | Ser | Val | Ala | Asn | Thr | Val | Thr | Val | Ser | Leu | |
| | 370 | | | | | 375 | | | | 380 | | | | | |
| Gln | Pro | Glu | Lys | Pro | Val | Val | Ser | Gly | Thr | Ala | Val | Thr | Leu | Ser | Leu |
| 385 | | | | | 390 | | | | | 395 | | | | | 400 |
| Pro | Ala | Val | Thr | Phe | Gly | Glu | Thr | Ser | Gly | Ala | Ala | Ile | Cys | Leu | Pro |
| | | | | 405 | | | | | 410 | | | | | 415 | |
| Ser | Val | Lys | Pro | Val | Val | Ser | Phe | Cys | Trp | Asp | His | Ile | Cys | Lys | Pro |
| | | | 420 | | | | | 425 | | | | | 430 | | |
| Val | Ile | Gly | Thr | Pro | Val | Gln | Ile | Lys | Leu | Ala | Gln | Pro | Gly | Pro | Val |
| | | 435 | | | | | 440 | | | | | 445 | | | |
| Leu | Ser | Gln | Pro | Ala | Gly | Ile | Pro | Thr | Gly | Ser | Ser | Ser | Lys | Gln | Leu |
| | 450 | | | | | 455 | | | | | 460 | | | | |
| Phe | Ser | Leu | Phe | His | Val | Val | Gln | Gln | Pro | Ser | Gly | Gly | Asn | Glu | Lys |
| 465 | | | | | 470 | | | | | 475 | | | | | 480 |
| Gln | Val | Thr | Thr | Ile | Ser | His | Ser | Ser | Thr | Leu | Thr | Ile | Gln | Lys | Cys |
| | | | | 485 | | | | | 490 | | | | | 495 | |
| Gly | Gln | Lys | Thr | Met | Pro | Val | Asn | Thr | Ile | Ile | Pro | Thr | Ser | Gln | Phe |
| | | | 500 | | | | | 505 | | | | | 510 | | |
| Pro | Pro | Ala | Ser | Ile | Leu | Lys | Gln | Ile | Thr | Leu | Pro | Gly | Asn | Lys | Ile |
| | | 515 | | | | | 520 | | | | | 525 | | | |
| Leu | Ser | Leu | Gln | Ala | Ser | Pro | Thr | Gln | Lys | Asn | Arg | Ile | Lys | Glu | Asn |
| | 530 | | | | | 535 | | | | | 540 | | | | |
| Val | Thr | Ser | Cys | Phe | Arg | Asp | Glu | Asp | Ile | Asn | Asp | Val | Thr | | Ser |
| 545 | | | | | 550 | | | | | 555 | | | | | 560 |
| Met | Ala | Gly | Val | Asn | Leu | Asn | Glu | Glu | Asn | Ala | Cys | Ile | Leu | Ala | Thr |
| | | | | 565 | | | | | 570 | | | | | 575 | |
| Asn | Ser | Glu | Leu | Val | Gly | Thr | Leu | Ile | Gln | Ser | Cys | Lys | Asp | Glu | Pro |
| | | | 580 | | | | | 585 | | | | | 590 | | |
| Phe | Leu | Phe | Ile | Gly | Ala | Leu | Gln | Lys | Arg | Ile | Leu | Asp | Ile | Gly | Lys |
| | | 595 | | | | | 600 | | | | | 605 | | | |
| Lys | His | Asp | Ile | Thr | Glu | Leu | Asn | Ser | Asp | Ala | Val | Asn | Leu | Ile | Ser |
| | 610 | | | | | 615 | | | | | 620 | | | | |
| Gln | Ala | Thr | Gln | Glu | Arg | Leu | Arg | Gly | Leu | Leu | Glu | Lys | Leu | Thr | Ala |
| 625 | | | | | 630 | | | | | 635 | | | | | 640 |
| Ile | Ala | Gln | His | Arg | Met | Thr | Thr | Tyr | Lys | Ala | Ser | Glu | Asn | Tyr | Ile |
| | | | | 645 | | | | | 650 | | | | | 655 | |
| Leu | Cys | Ser | Asp | Thr | Arg | Ser | Gln | Leu | Lys | Phe | Leu | Glu | Lys | Leu | Asp |
| | | | 660 | | | | | 665 | | | | | 670 | | |
| Gln | Leu | Glu | Lys | Gln | Arg | Lys | Asp | Leu | Glu | Glu | Arg | Glu | Met | Leu | Leu |
| | | 675 | | | | | 680 | | | | | 685 | | | |
| Lys | Ala | Ala | Lys | Ser | Arg | Ser | Asn | Lys | Glu | Asp | Pro | Glu | Gln | Leu | Arg |
| | 690 | | | | | 695 | | | | | 700 | | | | |
| Leu | Lys | Gln | Lys | Ala | Lys | Glu | Leu | Gln | Gln | Leu | Glu | Leu | Ala | Gln | Ile |
| 705 | | | | | 710 | | | | | 715 | | | | | 720 |
| Gln | His | Arg | Asp | Ala | Asn | Leu | Thr | Ala | Leu | Ala | Ala | Ile | Gly | Pro | Arg |
| | | | | 725 | | | | | 730 | | | | | 735 | |
| Lys | Lys | Arg | Pro | Leu | Glu | Ser | Gly | Ile | Glu | Gly | Leu | Lys | Asp | Asn | Leu |
| | | | 740 | | | | | 745 | | | | | 750 | | |
| Leu | Ala | Ser | Gly | Thr | Ser | Ser | Leu | Thr | Ala | Thr | Lys | Gln | Leu | His | Arg |
| | | 755 | | | | | 760 | | | | | 765 | | | |
| Pro | Arg | Ile | Thr | Arg | Ile | Cys | Leu | Arg | Asp | Leu | Ile | Phe | Cys | Met | Glu |
| | | 770 | | | | | 775 | | | | | 780 | | | |

```
Gln Glu Arg Glu Met Lys Tyr Ser Arg Ala Leu Tyr Leu Ala Leu Leu
785                 790                 795                 800
Lys
```

CELL-TYPE SPECIFIC TRANSCRIPTION FACTOR

FIELD OF THE INVENTION

The field of this invention is the regulation of cell specific genes.

BACKGROUND

The regulation of gene expression during development, differentiation and cell growth of metazoans is thought to be directed by a large number of different sequence specific DNA binding transcription factors. Extensive biochemical and genetic analysis carried out over the past decade reveals an elaborate cascade of protein-DNA and protein-protein transactions that collectively govern the levels of mRNA production. One key aspect of transcriptional regulation is the communication between enhancer bound gene specific activators and components of the basal apparatus. Recent studies have established that the transcription factor TFIID plays a critical role in receiving transcriptional activation signals from upstream enhancer and promoter binding factors and transducing them to the basal initiation complex.

The discovery that TFIID isolated from Drosophila and human cells consists of TBP and eight or more tightly associated subunits (TAFs) provided the first clue that perhaps TAFs can mediate transcriptional activation. Recent experiments have provided evidence that the activation domains of different upstream regulators can recognize and bind selectively to specific TAF subunits of the TFIID complex. More importantly, transcription reactions reconstituted with recombinant TAFs are able to provide coactivator function and thus potentiate enhancer dependent activation by sequence specific regulators. In addition, the assembly of partial TBP-TAF complexes suggested that specific activator-TAF interactions are required to direct both simple activation as well as synergistic transcription by multiple enhancer factors.

Several recent reports identified mammalian cell type specific cofactors that are required to implement activation of certain enhancer proteins (Sturbin et al., (1995) *Cell* 80, 497–506; Luo and Roeder (1995) *Mol & Cell. Biol* 15, 4115–4124). However, these cell type specific "coactivators" have been associated with activator complexes and were not part of the TFIID complex or the basal machinery.

Relevant Literature

Transcriptional activation has recently been reviewed by Tjian and Maniatis (1994) *Cell* 77, 5–8; Goodrich et al. (1996) *Cell* 84, 825–830; and Burley et al. (1996) *Annu Rev Biochem* 65, 769–799; see also references cited therein. Earlier references describing the isolation of TAFs include Dynlacht et al. (1991) *Cell* 66, 563–576 and Tanese et al. (1991) *Genes & Dev* 5, 2212–2224. Both hTAF$_{II}$130 and dTAF$_{II}$110 share sequence similarity with the disclosed hTAF$_{II}$105; see Tjian et al. (1996), U.S. Pat. No. 5,534,410 and Naoko Tanese (1996), unpublished hTAF$_{II}$130 sequence data.

SUMMARY OF THE INVENTION

The invention provides methods and compositions relating to a human tata-binding protein associated factor 105 (hTAF$_{II}$105), related nucleic acids, and protein domains thereof having hTAF$_{II}$105-specific activity. The proteins may be produced recombinantly from transformed host cells from the subject hTAF$_{II}$105 encoding nucleic acids or purified from human cells. The invention provides isolated hTAF$_{II}$105 hybridization probes and primers capable of specifically hybridizing with the disclosed hTAF$_{II}$105 gene, hTAF$_{II}$105-specific binding agents such as specific antibodies, and methods of making and using the subject compositions in diagnosis (e.g. genetic hybridization screens for hTAF$_{II}$105 transcripts), therapy (e.g. gene therapy to modulate hTAF$_{II}$105 gene expression) and in the biopharmaceutical industry (e.g. as immunogens, reagents for isolating B-cell specific activators or other transcriptional regulators, reagents for screening chemical libraries for lead pharmacological agents, etc.).

DETAILED DESCRIPTION OF THE INVENTION

The nucleotide sequence of a natural cDNA encoding an hTAF$_{II}$105 protein is shown as SEQ ID NO:1 and the full conceptual translate shown as SEQ ID NO:2. The hTAF$_{II}$105 proteins of the invention include incomplete translates of SEQ ID NO:1 and deletion mutants of SEQ ID NO:2, which translates and deletion routants have hTAF$_{II}$105-specific amino acid sequence and binding specificity or function. Such active hTAF$_{II}$105 deletion mutants, hTAF$_{II}$105 peptides or protein domains comprise at least 20, preferably at least about 40, more preferably at least about 80 consecutive residues of SEQ ID NO:2. For examples, the hTAF$_{II}$105 protein domain consisting of residues 547–801 is shown to provide TAF-binding function and the domain consisting of residues 1–546 is shown to provide activator binding function, inter alia, in solid-phase binding assays as described below.

hTAF$_{II}$105-specific activity or function may be determined by convenient in vitro, cell-based, or in vivo assays: e.g. in vitro binding assays, cell culture assays, in animals (e.g. immune response, gene therapy, transgenics, etc.), etc. Binding assays encompass any assay where the molecular interaction of an hTAF$_{II}$105 protein with a binding target is evaluated. The binding target may be a natural intracellular binding target such as another TAF or other component of TFIID, a specific transcriptional activator, an hTAF$_{II}$ 105 substrate or nucleic acid binding site or other regulator that directly modulates hTAF$_{II}$ 105 activity or its localization; or non-natural binding target such a specific immune protein such as an antibody, or an hTAF$_{II}$105 specific agent such as those identified in screening assays such as described below. hTAF$_{II}$105-binding specificity may assayed by binding equilibrium constants (usually at least about $10^7 M^{-1}$, preferably at least about $10^8 M^{-1}$, more preferably at least about $10^9 M^{-1}$), by the ability of the subject protein to function as negative mutants in hTAF$_{II}$105-expressing cells, to elicit hTAF$_{II}$105 specific antibody in a heterologous host (e.g a rodent or rabbit), etc. In any event, the hTAF$_{II}$105 binding specificity of the subject hTAF$_{II}$105 proteins necessarily distinguishes other natural human proteins including hTAF$_{II}$130.

The claimed hTAF$_{II}$105 proteins are isolated or pure: an "isolated" protein is unaccompanied by at least some of the material with which it is associated in its natural state, preferably constituting at least about 0.5%, and more preferably at least about 5% by weight of the total protein in a given sample and a pure protein constitutes at least about 90%, and preferably at least about 99% by weight of the total protein in a given sample. The hTAF$_{II}$105 proteins and protein domains may be synthesized, produced by recombinant technology, or purified from human cells. A wide variety of molecular and biochemical methods are available for biochemical synthesis, molecular expression and purification of the subject compositions, see e.g. Molecular Cloning, A Laboratory Manual (Sambrook, et al. Cold Spring Harbor Laboratory), Current Protocols in Molecular Biology (Eds. Ausubel, et al., Greene Publ. Assoc., Wiley-Interscience, NY) or that are otherwise known in the art.

The invention provides natural and non-natural hTAF$_{II}$105-specific binding agents, methods of identifying and making such agents, and their use in diagnosis, therapy and pharmaceutical development. For example, hTAF$_{II}$105-specific agents are useful in a variety of diagnostic and therapeutic applications. Novel hTAF$_{II}$105-specific binding agents include hTAF$_{II}$105-specific receptors, such as somatically recombined protein receptors like specific antibodies or T-cell antigen receptors (see, e.g Harlow and Lane (1988) Antibodies, A Laboratory Manual, Cold Spring Harbor Laboratory) and other natural intracellular binding agents identified with assays such as one-, two- and three-hybrid screens, non-natural intraceliular binding agents identified in screens of chemical libraries such as described below, etc. For diagnostic uses, the binding agents are frequently labeled, such as with fluorescent, radioactive, chemiluminescent, or other easily detectable molecules, either conjugated directly to the binding agent or conjugated to a probe specific for the binding agent. Agents of particular interest modulate hTAF$_{II}$105 function, e.g. hTAF$_{II}$105-dependent transcriptional activation; for example, isolated cells, whole tissues, or individuals may be treated with an hTAF$_{II}$105 binding agent to activate, inhibit, or alter hTAF$_{II}$105-dependent transcriptional processes.

The amino acid sequences of the disclosed hTAF$_{II}$105 proteins are used to back-translate hTAF$_{II}$105 protein-encoding nucleic acids optimized for selected expression systems (Holler et al. (1993) Gene 136, 323–328; Martin et al. (1995) Gene 154, 150–166) or used to generate degenerate oligonucleotide primers and probes for use in the isolation of natural hTAF$_{II}$105-encoding nucleic acid sequences ("GCG" software, Genetics Computer Group, Inc, Madison Wis.). hTAF$_{II}$105-encoding nucleic acids used in hTAF$_{II}$105-expression vectors and incorporated into recombinant host cells, e.g. for expression and screening, transgenic animals, e.g. for functional studies such as the efficacy of candidate drugs for disease associated with hTAF$_{II}$105-mediated signal transduction, etc.

The invention also provides nucleic acid hybridization probes and replication/amplification primers having a hTAF$_{II}$105 cDNA specific sequence contained in SEQ ID NO:1 and sufficient to effect specific hybridization thereto (i.e. specifically hybridize with SEQ ID NO:1 in the presence of human B-cell cDNA). Such primers or probes are at least 12, preferably at least 24, more preferably at least 36 and most preferably at least 96 bases in length. Demonstrating specific hybridization generally requires stringent conditions, for example, hybridizing in a buffer comprising 30% formanaide in 5×SSPE (0.18M NaCl, 0.01M NaPO$_4$, pH 7.7, 0.001M EDTA) buffer at a temperature of 42° C. and remaining bound when subject to washing at 42° C. with 0.2×SSPE; preferably hybridizing in a buffer comprising 50% formamide in 5×SSPE buffer at a temperature of 42° C. and remaining bound when subject to washing at 42° C. with 0.2×SSPE buffer at 42° C. hTAF$_{II}$105 cDNA homologs can also be distinguished from other protein using alignment algorithms, such as BLASTX (Altschul et al. (1990) Basic Local Alignment Search Tool, J Mol Biol 215, 403–410).

The subject nucleic acids are of synthetic/non-natural sequences and/or are isolated, i.e. unaccompanied by at least some of the material with which it is associated in its natural state, preferably constituting at least about 0.5%, preferably at least about 5% by weight of total nucleic acid present in a given fraction, and usually recombinant, meaning they comprise a non-natural sequence or a natural sequence joined to nucleotide(s) other than that which it is joined to on a natural chromosome. Nucleic acids comprising the nucleotide sequence of SEQ ID NO:1 or fragments thereof, contain such sequence or fragment at a terminus, immediately flanked by a sequence other than that which it is joined to on a natural chromosome, or flanked by a native flanking region fewer than 10 kb, preferably fewer than 2 kb, which is at a terminus or is immediately flanked by a sequence other than that which it is joined to on a natural chromosome. While the nucleic acids are usually RNA or DNA, it is often advantageous to use nucleic acids comprising other bases or nucleotide analogs to provide modified stability, etc.

The subject nucleie acids find a wide variety of applications including use as translatable transcripts, hybridization probes, PCR primers, diagnostic nucleic acids, etc.; use in detecting the presence of hTAF$_{II}$105 genes and gene transcripts and in detecting or amplifying nucleic acids encoding additional hTAF$_{II}$105 homologs and structural analogs. In diagnosis, hTAF$_{II}$105 hybridization probes find use in identifying wild-type and mutant hTAF$_{II}$105 alleles in clinical and laboratory samples. Mutant alleles are used to generate allele-specific oligonucleotide (ASO) probes for high-throughput clinical diagnoses. In therapy, therapeutic hTAF$_{II}$105 nucleic acids are used to modulate cellular expression or intracellular concentration or availability of active hTAF$_{II}$105.

The invention provides efficient methods of identifying agents, compounds or lead compounds for agents active at the level of a hTAF$_{II}$105 modulatable cellular function. Generally, these screening methods involve assaying for compounds which modulate hTAF$_{II}$105 interaction with a natural hTAF$_{II}$105 binding target. A wide variety of assays for binding agents are provided including labeled in vitro protein-protein binding assays, immunoassays, cell based assays, etc. The methods are amenable to automated, cost-effective high throughput screening of chemical libraries for lead compounds. Identified reagents find use in the pharmaceutical industries for animal and human trials; for example, the reagents may be derivatized and rescreened in in vitro and in vivo assays to optimize activity and minimize toxicity for pharmaceutical development. Target indications include B-cell proliferative disease, inflammation, hypersensitivity, etc. Alternatively, agents which enhance hTAF$_{II}$105 transcriptional activation may be selected for indications where the enhancement of B-cell differentiation is desirable, e.g. immune deficiencies, infection, etc.

In vitro binding assays employ a mixture of components including an hTAF$_{II}$105 protein, which may be part of a fusion product with another peptide or polypeptide, e.g. a tag for detection or anchoring, etc. The assay mixtures comprise a natural intracellular hTAF$_{II}$105 binding target. While native binding targets may be used, it is frequently preferred to use portions (e.g. peptides) thereof so long as the portion provides binding affinity and avidity to the subject hTAF$_{II}$105 protein conveniently measurable in the assay. The assay mixture also comprises a candidate pharmacological agent. Candidate agents encompass numerous chemical classes, though typically they are organic compounds; preferably small organic compounds and are obtained from a wide variety of sources including libraries of synthetic or natural compounds. A variety of other reagents may also be included in the mixture. These include reagents like salts, buffers, neutral proteins, e.g. albumin, detergents, protease inhibitors, nuclease inhibitors, antimicrobial agents, etc. may be used.

The resultant mixture is incubated under conditions whereby, but for the presence of the candidate pharmacological agent, the hTAF$_{II}$105 protein specifically binds the cellular binding target, portion or analog with a reference binding affinity. The mixture components can be added in any order that provides for the requisite bindings and incubations may be performed at any temperature which facilitates optimal binding. Incubation periods are likewise selected for optimal binding but also minimized to facilitate rapid, high-throughput screening.

After incubation, the agent-biased binding between the hTAF$_{II}$105 protein and one or more binding targets is detected by any convenient way. For cell-free binding type assays, a separation step is often used to separate bound from unbound components. Separation may be effected by precipitation (e.g. TCA precipitation, immunoprecipitation, etc.), immobilization (e.g on a solid substrate), etc., followed by washing by, for examples, membrane filtration (e.g. Whatman's P-81 ion exchange paper, Polyfiltronic's hydrophobic GFC membrane, etc.), gel chromatography (e.g. gel filtration, affinity, etc.). For hTAF$_{II}$105-dependent transcription assays, binding is detected by a change in the expression of an hTAF$_{II}$105-dependent reporter.

Detection may be effected in any convenient way. For cell-free binding assays, one of the components usually comprises or is coupled to a label. The label may provide for direct detection as radioactivity, luminescence, optical or electron density, etc. or indirect detection such as an epitope tag, an enzyme, etc. A variety of methods may be used to detect the label depending on the nature of the label and other assay components, e.g. through optical or electron density, radiative emissions, nonradiative energy transfers, etc. or indirectly detected with antibody conjugates, etc.

A difference in the binding affinity of the hTAF$_{II}$105 protein to the target in the absence of the agent as compared with the binding affinity in the presence of the agent indicates that the agent modulates the binding of the hTAF$_{II}$105 protein to the hTAF$_{II}$105 binding target. Analogously, in the cell-based transcription assay also described below, a difference in the hTAF$_{II}$105 transcriptional induction in the presence and absence of an agent indicates the agent modulates hTAF$_{II}$105-induced transcription. A difference, as used herein, is statistically significant and preferably represents at least a 50%, more preferably at least a 90% difference.

The following examples are offered by way of illustration and not by way of limitation.

EXPERIMENTAL

1. TFIID subunits in different human cell types

To test the possibility that some TFIID subunits might be cell type specific, we compared the composition of TBP-TAF complexes isolated from several human cell lines representing different tissues. For this purpose, nuclear extracts were first fractionated by phosphocellulose (PC) chromatography to separate TFIID from other TBP-TAF complexes (i.e. SL1 and TFIIIB). The resulting 1.0M NaCl PC fractions were subjected to anti-TBP affinity purification followed by SDS-PAGE analysis and staining with silver. As expected, the subunit composition and levels of the core TAFs relative to TBP were very similar among the different cell types examined. By contrast, the TFIID complex isolated from Daudi B cells contained an additional polypeptide of approximately 105 kDa that consistently coimmunoprecipitated with anti-TBP antibodies. This novel polypeptide is barely detectable in TFIID isolated from non B cells such as the neuroblastoma SK-N, glioblastoma U87, Jurkat and Hut78 T cells and HeLa cervical carcinoma.

Association of this 105 kDa polypeptide with the TBP/TAFs complex appears to be specific as it can be coimmunoprecipitated with TFIID using a different TBP antibody but not by mock immunoprecipitation in the absence of TBP antibodies. We confirmed that the 105 Kd polypeptide is not a breakdown product of either TAF250 or TAF$_{II}$130 by western blot analysis using either anti-TAF$_{II}$250 or anti-TAF$_{II}$130 antibodies.

Daudi cells are characterized as Epstein Barr virus positive (EBV$^+$), differentiated, IgG producing B cells. To determine whether the association of p105 with TBP is either EBV or differentiation related, we isolated TFIID from a less differentiated, EBV$^+$B cell, Jy, and found insignificant amounts of p105 relative to the other TFIID subunits indicating that EBV gone expression is not responsible for the high levels of p105 found in TFIID isolated from Daudi cells. Therefore, we conclude that this 105 kDa protein is a TAF that becomes specifically associated with TFIID in highly differentiated B cells.

2. hTAF$_{II}$105 is a substoichiometric subunit of TFIID

In order to obtain independent evidence that the TAF$_{II}$105 protein is selectively associated with TFIID rather than SL1 and TFIIIB, we have used a monoclonal antibody directed against human TAF$_{II}$130 to isolate TFIID complexes from either Daudi B or Jurkat T cells. For these experiments, we used unfractionated nuclear extracts rather than the 1.0M NaCl PC fraction enriched for TFIID to exclude the possibility that TAF$_{II}$105-containing complexes isolated from different cell types might merely reflect differential chromatographic properties. Both TBP and TAF$_{II}$130 antibodies coimmunoprecipitated TAF$_{II}$105 together with the other "core" TFIID subunits from Daudi nuclear extract. By contrast, only TBP and the core TAFs were isolated by TAF$_{II}$130 antibody from Jurkat nuclear extracts. To confirm these results, we also performed immunoprecipitation using the PC 1.0M NaCl fraction from Daudi and Jurkat cell extracts. As expected, anti-TBP selectively precipitated the TAF$_{II}$105 subunit from Daudi cells but not from Jurkat cells. These results indicate that TAF$_{II}$105 is a novel TAF subunit that is only found associated with TFIID in selected cell types such as highly differenffated B cells.

We hypothesized that a TFIID complex containing a putative cell type specific subunit would most likely participate in transcription of only a limited subset of genes, perhaps cell type specific genes. Consequently, one might expect that only a subset of TFIID complexes within the cell will contain this subunit. Became silver staining of proteins is notoriously non-quantitative, we have attempted to determine the relative stoichiometry of TAF$_{II}$105 in the B cell TFIID complex by more reliable staining methods. Antibody affinity purified TFIID complexes isolated from Daudi cells were subjected to SDS-PAGE and stained both by silver and Coomassie blue. Unlike the intense band of TAF$_{II}$105 observed by silver staining, the Coomassie stained TAF$_{II}$105 revealed that it is present in approximately 10 fold lower levels relative to the core TAFs and TBP. The apparent substoichiometric amounts of TAF$_{II}$105 was further confirmed by two additional protein staining techniques, ponceau S and Zinc staining. These results indicate that only a small fraction (~5–10%) of the TFIID complexes within B cells contain TAF$_{II}$105.

3. hTAF$_{II}$105 is a homolog of Drosophila TAF$_{II}$110 and human TAF$_{II}$130

In order to further characterize this candidate cell type specific TAF, we set out to isolate the corresponding cDNA.

For this purpose, we purified TFIID from nuclear extracts prepared from 2000 liters of Daudi cells. TFIID was first fractionated over a phosphocellulose column followed by anti-TBP affinity chromatography. The TFIID polypeptides were resolved on a preparative SDS-PAGE gel, transferred onto nitrocellulose membrane and the band corresponding to hTAF$_{II}$105 was excised and digested with either trypsin or S. aureus V8 protease. The resulting peptides were separated by reversed phase HPLC and subjected to microsequence analysis. The amino acid sequence of several peptides revealed striking similarities to the conserved C-terminal region of dTAF$_{II}$110 and its human homolog TAF$_{II}$130. We, therefore, screened a Daudi cDNA library with a DNA fragment encompassing a highly conserved region of hTAF$_{II}$130 under low stringency hybridization conditions. Two cDNA clones of approximately 2 kb corresponding to TAF$_{II}$105 were obtained. These cDNAs contained a 3' poly(A) tail and a portion of the coding region of TAF$_{II}$105. To isolate the remaining portions of TAF$_{II}$105 we screened several additional human cDNA libraries with TAF$_{II}$105 specific probes. Two additional clones were isolated, one of 1.6 Kb and the other of 3.6 Kb that overlapped the 3' region. DNA sequence analysis of the 3.6 Kb insert revealed an open reading frame of 2406 bp that included all the peptide sequences obtained from the proteolytic digestions. When this long cDNA was expressed in Sf9 cells with a flag-tag, the size of the recombinant protein was very similar to the endogenous TAF$_{II}$105. However, since this clone does not contain a methionine residue that is preceded by a stop codon at its most 5' region, it appears to encode a deletion mutant of the native TAF$_{II}$105 (we estimate a 5–10 residue N-terminal truncation).

Amino acid sequence deduced from the cDNA revealed several regions with a high degree of similarity to hTAF$_{II}$130 and dTAF$_{II}$110. In particular, the C-terminal ⅓ of these proteins that includes domains involved in binding to other TAFs, is highly conserved (68% identity and 87% homology). However, the majority of the sequences in the N-terminal region were quite diverged indicating that hTAF$_{II}$105 has evolved the ability to interact with a different subset of activators than those targeted by hTAF$_{II}$130 and dTAF$_{II}$110. In particular, functional studies as described below demonstrate that the less conserved N-terminal domain of TAF$_{II}$105 contains interaction surfaces that bind to activators in differentiating B cells.

4. TAF$_{II}$105 and dTAF$_{II}$110 share conserved interfaces for interacting with other TFIID subunits Extensive analysis of the cloned TFIID subunits indicated that formation of a stable TFIID complex involves multiple TAF-TBP and TAF-TAF interactions. To identify the subunits in TFIID that contact TAF$_{II}$105, we performed a series of protein:protein interaction assays using immobilized flag-tagged TAF$_{II}$105 and 35S-labeled in vitro translated TFIID subunits. These experiments indicate that TAF$_{II}$105 specifically interacts with hTAF$_{II}$250, dTAF$_{II}$150, the large subunit of TFIIA, and weakly with TBP. In contrast, TAF$_{II}$105 did not appear to interact specifically with dTAF$_{II}$80, hTAF$_{II}$70, TAF$_{II}$60, dTAF$_{II}$40, hTAF$_{II}$32, dTAF$_{II}$30α and dTAF$_{II}$30β. Interestingly, a similar pattern of selective protein interactions have been observed for dTAF$_{II}$110 indicating that these closely related TAFs have conserved interaction surfaces (i.e. C-terminus) for incorporating into the TFIID complex. An exception to this pattern of TAF:TAF interaction is the ability of dTAF$_{II}$110 to bind TAF$_{II}$30α. In addition, dTAF$_{II}$110 and TAF$_{II}$105 can interact with each other to form dimers and heterodimers.

5. Cell type specific association of TAF$_{II}$105 with TFIID is post transcriptionally regulated.

To address potential mechanisms of TAF$_{II}$105 regulation, the levels of its mRNA in different cell types were determined by northern blot analysis with a TAF$_{II}$105 specific probe. As a control, identical samples were hybridized with the ubiquitous hTAF$_{II}$130 probe. Our analysis of TAF$_{II}$105 RNA revealed a single transcript of about 4.6 Kb that is expressed at relatively invariant levels in all the cell types examined. To further confirm this finding, we performed RNase protection assays. Similar amounts of RNA extracted from different cell types were hybridize with hTAF$_{II}$105 or hTAF$_{II}$250 specific probes followed by digestion with RNase A and RNase T1. Here again, the levels of protected TAF$_{II}$105 transcripts from different cell types appeared comparable. Taken together these data indicate that TAF$_{II}$105 may be post-transcriptionally regulated in a cell type specific manner.

To quantitate the amounts of TAF$_{II}$105 protein in different cells, we expressed the less conserved N-terminal portion of the protein in E. coli and raised polyclonal antibodies against this region of TAF$_{II}$105. These anti-TAF$_{II}$105 antibodies specifically recognize a 105 Kd polypeptide present in Daudi nuclear extract as well as recombinant TAF$_{II}$105 produced in Sf9 cells. As expected, anti-TAF$_{II}$105 antibodies can also immunoprecipitate TAF$_{II}$105 together with all the core TFIID subunits including its homolog TAF$_{II}$130 from Daudi extracts indicating that both, TAF$_{II}$105 and TAF$_{II}$130, might be present in the same complex. To measure the relative levels of TAF$_{II}$105 protein expressed in different cell types, similar amounts of nuclear extracts from different cell types were subjected to Western blot analysis using TAF$_{II}$105 and TBP antibodies. The levels of TAF$_{II}$105 protein are significantly higher in Daudi B cells than in non B cells suggesting that the cell type specific regulation of TAF$_{II}$105 may be, in part, at the level of protein expression. Next, the anti-TAF$_{II}$105 antibodies were used to compare the levels of TAF$_{II}$105 associated with affinity purified TFIID isolated from either Daudi or HeLa cells. These antibodies specifically detected TAF$_{II}$105 in Daudi TFIID but not in HeLa TFIID. We verified that the levels of TBP and the core TAFs in the TFIID complex were similar by silver staining and by Western blotting with TBP antibodies. These results taken together indicate that both, the production of TAF$_{II}$105 protein and its association with TFIID are cell type specifically regulated.

6. Experimental Procedures a) Antibodies and immunoprecipitations

Nuclear extracts from different cell types were prepared and fractionated by phosphocellulose P11 column (PC) as described (Tanese et al., 1991 *Genes & Dev.* 5, 2212–2224). Polyclonal anti-TBP antibodies raised against recombinant hTBP were described (Tanese et al., supra). The antibodies were affinity purified using TBP-coupled affinity resins Monoclonal anti-TAF$_{II}$130 antibody IA5 was described (Ruppert et al., 1993, *Nature* 362, 175–179). TAF$_{II}$105 polyclonal antibodies were raised against recombinant protein corresponding to amino acid 1-552 produced in bacteria with 6 histidine-tag. The inclusion bodies containing overexpressed TAF$_{II}$105 were dissolved in 6M urea, purified by Ni$^+$ agarose resin, resolved on SDS-PAGE and TAF$_{II}$105 protein was excised and injected into rabbits. Immunoprecipitations of TFIID complex by affinity purified TBP antibodies, anti-TAF$_{II}$130 (IA5) and anti-TAF$_{II}$105 were carried with TFIID enriched PC fractions or directly from nuclear extracts essentially as described (Tanese et al., supra). Briefly, 400 μg of 1.0M NaCl PC fraction or 5 mg of nuclear extracts in HEMG buffer (20 mM Hepes 7.9, 100 mM KCl, 12.5 mM MgCl$_2$, 0.2 mM EDTA, 0.1% NP-40, 1 mM DTT, 0.2 mm PMSF) were incubated with antibodies and protein A sepharose beads at 4° C. for 2–3 hours. The immune complexes were washed with HEMG buffer 5 times and eluted either by 1M guanidine-HCl followed by TCA precipitation or by 5 minutes boiling in SDS-PAGE protein sample buffer.

b) Cloning of $TAF_{II}105$ cDNA

Daudi cells nuclear extracts were prepared from 2000 liters of culture and TFIID enriched fraction was obtained by PC column (Tanese et al., 1991, supra). TFIID was immunopurified directly from PC 1.0M NaCl fraction using crosslinked anti-TBP resin and the TAFs were eluted by 50 mM glycine pH 2.5, 150 mM NaCl and precipitated with trichloroacetic acid (TCA) containing deoxycholate (4 mg/ml). The TAFs were resolved by SDS-PAGE, transferred to nitrocellulose membrane and stained with ponceau S (Sigma). The band corresponding to $TAF_{II}105$ was excised, digested with either trypsin or V8 proteases and peptides eluted from the membrane were resolved by reversed-phase HPLC and subjected to microsequencing. Daudi cDNA library ($1.5 \times 10^6$ phages) was screened with 237 bp probe derived from $hTAF_{II}130$ generated by PCR. 2 $TAF_{II}105$ positive phages were isolated, their 1.9 and 2 kb inserts were cloned into Bluescript $KS^+$ (Stratagene), sequenced and found to contain a 1 kb of 3' untranslated region and 1 kb coding region containing the sequence of 7 peptides obtained by the proteolytic digestion. To clone the N-terminus of $TAF_{II}105$, the following human cDNA libraries were screened: human tertocarcinoma, Jurkat, HeLa and another Daudi cDNA library. 2 positive clones were obtained from the HeLa cell library, one of 1.6 Kb overlapping with the clones isolated from the Daudi library and a second clone of 3.6 Kb insert. This insert was cloned in Bluescript KS+ and both strands of this cDNA were completely sequenced with Bluescript or $TAF_{II}105$ specific primers.

c) RNA analysis

Total cytoplasmic RNA samples were prepared from cultured cells according to the procedure that has been described (Gough, 1988, *Analytical Biochemistry* 1 73, 93–95). For Northern blot analysis, 30 μg of RNA prepared from different cell types were electrophoresed on a 1% formaldehyde/agarose gel in duplicates. RNA was transferred to nitrocellulose membrane and hybridized with riboprobes complementary to either $hTAF_{II}105$ or $hTAF_{II}130$. For RNase protection assay, 30 μg of total RNA extracted from different cell types were hybridized with anti-sense RNA probes corresponding to $hTAF_{II}105$ or $hTAF_{II}250$ for 16 hours at 55° C. in 40 mm PIPES pH 6.7, 350 mM NaCl, 1 mM EDTA and 80% formamide. RNase A (40 μg/ml) and RNase T1 (2 μg/ml) were added and digestion was carried out at 30° C. for 30 minutes. The reactions were terminated bit the addition of 50 μg of proteinase K, 10 μl of SDS and incubation at 37° C. for 30 minutes. After phenolchloroform extraction and ethanol precipitation the samples were resolved on 6% denaturing polyacrylamide gel and autoradiographed.

d) Expression of $TAF_{II}105$ protein

A 3.6 kb NotI fragment containing the entire sequences of the long cDNA was subcloned into the NotI site of the vector pVL1392. Next, a 3.1 kb NdeI fragment containing the coding region was subcloned into the baculovirus expression vector pVLSG2Flag in NdeI site. Crude extracts from cells expressing flag-$TAF_{II}105$ were bound to flag antibody beads (Kodak) in 0.5M KCl HEMG buffer for 2–3 hours. After 5 washes with the same buffer a small portion was analysed by SDS-PAGE. Before the interaction assays the beads were washed twice with 0.1M KCl HEMG.

e) In vitro binding experiments $^{35}$S-labeled TAFs were synthesized in vitro by T7 RNA polymerase and rabbit reticulocytes lysate and incubated with flag beads or with $TAF_{II}105$ coupled to flag beads in 0.1M KCl HEMG buffer for 2 hours at 4° C. The beads were washed 5 times with the same buffer and the bound proteins were eluted by 5 minutes boiling in protein sample buffer followed by SDS-PAGE and autoradiography.

EXAMPLES

1. Protocol for $hTAF_{II}105$-$hTAF_{II}250$ binding assay.

A solid phase bead-based TAF interaction assay uses immobilized flag-tagged $hTAF_{II}105$ and $^{35}$S-labeled in vitro translated $hTAF_{II}250$ subunit. The $hTAF_{II}250$ subunit was translated in vitro by rabbit reticulocyte lysate in the presence of 355-methionine. Labeled $hTAF_{II}250$ was used in interaction assays with immobilized flag-tagged $hTAF_{II}105$. As a control the labeled TAF was incubated with flag beads in the absence of $hTAF_{II}105$ protein. The beads were eluted, resolved on SDS-PAGE and autoradiographed. The input represented 10% of the labeled protein used for the interaction assay.

2. Protocol for high throughput $hTAF_{II}105$-TFIIA large subunit complex formation assay.

A. Reagents:

Neutralitc Avidin: 20 μg/ml in PBS.

Blocking buffer: 5% BSA, 0.5% Tween 20 in PBS; 1 hour at room temperature.

Assay Buffer: 100 mM KCl, 20 mM HEPES pH 7.6, 1 mM $MgCl_2$, 1% glycerol, 0.5% NP-40, 50 mM β-mercaptoethanol, 1 mg/ml BSA, cocktail of protease inhibitors.

$^{33}$P $hTAF_{II}105$ protein 10x stock: $10^{-8}$–$10^{-6}$M "cold" $hTAF_{II}105$ subunit supplemented with 200,000–250,000 cpm of labeled $hTAF_{II}105$ (Beckman counter). Place in the 4° C. microfridge during screening.

Protease inhibitor cocktail (1000X): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2 mM $NaVo_3$ (Sigma #S-6508) in 10 ml of PBS.

hTFIIA large subunit: $10^{-7}$–$10^{-5}$M biotinylated hTFIIA large subunit in PBS.

B. Preparation of assay plates:

Coat with 120 μl of stock N-Avidin per well overnight at 4° C.

Wash 2 times with 200 μl PBS.

Block with 150 μl of blocking buffer.

Wash 2 times with 200 μl PBS.

C. Assay:

Add 40 μl assay buffer/well.

Add 10 μl compound or extract.

Add 10 μl $^{33}$P-$hTAF_{II}105$ protein (20,000–25,000 cpm/ 0.1–10 pmoles/well=$10^{-9}$–$10^{-7}$M final concentration).

Shake at 25° C. for 15 minutes.

Incubate additional 45 minutes at 25° C.

Add 40 μl biotinylated hTFII subunit (0.1–10 pmoles/40 ul in assay buffer)

Incubate 1 hour at room temperature.

Stop the reaction by washing 4 times with 200 μl PBS.

Add 150 μl scintillation cocktail.

Count in Topcount.

D. Controls for all assays (located on each plate):
a. Non-specific binding
b. Soluble (non-biotinylated hTAF$_{II}$105) at 80% inhibition.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A recombinant nucleic acid encoding a human tata-binding protein associated factor (hTAF$_{II}$105 protein (SEQ ID NO:2), or an hTAF$_{II}$105 protein deletion mutant thereof having at least 20 consecutive amino acids of SEQ ID NO:2 and said deletion mutant specifically binds at least one of hTAF$_{II}$250, hTAF$_{II}$150, TFIIA or a hTAF$_{II}$105-specific antibody.

2. A recombinant nucleic acid according to claim 1, wherein said deletion mutant comprises at least 40 consecutive amino acids of SEQ ID NO:2.

3. A recombinant nucleic acid according to claim 1, wherein said deletion mutant comprises at least SEQ ID NO:2, residues 547–801.

4. A recombinant nucleic acid according to claim 1, wherein said deletion mutant comprises at least SEQ ID NO:2, residues 1–546.

5. An isolated hTAF$_{II}$105 nucleic acid comprising SEQ ID NO:1, or a fragment thereof having at least 24 consecutive bases of SEQ ID NO:1 and sufficient to specifically hybridize with a nucleic acid having the sequence defined by SEQ ID NO:1 in the presence of human genomic DNA.

6. An isolated hTAF$_{II}$105 nucleic acid comprising SEQ ID NO:1, or a fragment thereof having at least 24 consecutive bases of SEQ ID NO:1 and sufficient to specifically hybridize with a nucleic acid having the sequence defined by SEQ ID NO:1 in the presence of human B cell cDNA.

7. An isolated hTAF$_{II}$105 nucleic acid according to claim 6, comprising SEQ ID NO:1.

8. A cell comprising a nucleic acid according to claim 1.

9. A cell comprising a nucleic acid according to claim 3.

10. A cell comprising a nucleic acid according to claim 4.

11. A method of making an isolated hTAF$_{II}$105 protein, comprising steps: introducing a nucleic acid according to claim 1 into a host cell or cellular extract, incubating said host cell or extract under conditions whereby said nucleic acid is expressed as a transcript and said transcript is expressed as a translation product comprising said protein, and isolating said translation product.

12. A method according to claim 11, wherein said introducing step comprises introducing nucleic acid according to claim 3.

13. A method according to claim 11, wherein said introducing step comprises introducing a nucleic acid according to claim 4.

* * * * *